US00PP11171P

United States Patent [19]

Pouw

[11] Patent Number: Plant 11,171

[45] Date of Patent: Jan. 4, 2000

[54] HYBRID TEA ROSE PLANT NAMED 'PANSOMRO'

[75] Inventor: A. A. Pouw, De Kwakel, Netherlands

[73] Assignee: Panorama Roses N.V., Curacao, Netherlands

[21] Appl. No.: 08/982,491

[22] Filed: Dec. 2, 1997

[51] Int. Cl.[7] ..... A01H 5/00

[52] U.S. Cl. ..... Plt./130

[58] Field of Search ..... Plt./11, 12, 13, Plt./18, 19, 130, 131, 132, 141, 142, 143

*Primary Examiner*—Howard J. Locker

*Attorney, Agent, or Firm*—Christie, Parker & Hale, LLP

[57] ABSTRACT

A new variety of hybrid tea rose plant producing pink blend flowers of good form and suitable for growing under glass.

1 Drawing Sheet

BACKGROUND OF THE INVENTION

The present invention relates to a new and distinct variety of rose plant of the hybrid tea rose class which was created by crossing undistributed, unnamed and unpatented seedlings as seed and pollen parents in Quito, Ecuador. The varietal denomination of the new variety is 'PANSOMRO'. The new variety was isolated and asexually reproduced by budding in Quito, Ecuador.

SUMMARY OF THE INVENTION

Among the novel characteristics possessed by this new variety which distinguish it from its parents and all other varieties of which I am aware are its attractive pink blend flowers with long stems borne on a floriferous plant and suitable for production of cut flowers under glass.

Asexual reproduction by budding of the new variety as performed in Quito, Ecuador, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATION

The accompanying illustration shows a typical specimen of the vegetative growth and flowers of the new variety as a cut flower, depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings. Class: Hybrid Tea.

The following further horticultural description is based on observations made of specimens grown under glass in Quito, Ecuador.

FLOWER

Blooming habit: Nearly continous; under glass in The Netherlands about 140 stems/$m^2$/year; stem length about 0.6 m to 1 m .

A. Bud:

(1) *Size.*—Medium, about 3 to 4 cm long by about 2 cm wide, before sepals fall. About 4 cm long by about 3 to 4 cm wide, after sepals separate further.

(2) *Form.*—Ovate (shape of longitudinal section just before separation of sepals); urn-shaped after sepals part and petals begin to separate.

(3) *Color.*—Before sepals separate, near 45A at petal edge becoming lighter until become near 9A at point of petal attachment.

(4) *Sepals.*—About same length as bud, some slightly foliaceous; but most not, near 138B on top surface, near 138D on undersurface.

(5) *Peduncle.*—Strength-erect, about 6 cm. Color-brownish green, near 137C to 137D with brownish tinge, none to few hairs or prickles.

B. Flower: Medium; viewed from above — star-shaped; viewed from side — (a) upper part of fully opened flower, flattened convex; (b) lower part of fully opened flower, flattened convex.

(1) *Size.*—Average size when fully expanded — about 12 to 13 cm at about full open.

(2) *Borne.*—Singly, one to a stem.

(3) *Form.*—Pointed center, spiral imbricated, some outer petals reflex to points, some inner petals reflex to points and some roll under; flat top.

(4) *Petalage.*—Fully double.

(5) *Color.*—After sepals part and petals unfurl color of petal top surface near edges appears near 45A but quickly washed with light pink, near 55C, and near white with yellow cast and shows veining, near 2B to 2C; center of flower where petals bunch shows near 45A but outer petals show white washing at petals below edge. Petal undersurface exhibits red edge marginal zone near 46A and 46B and the middle zone near 36A. Color at point of petal attachment is near 9B. Overall tonality from a distance is unusual pink blend with red center and red/silvery white outer petals.

(6) *Peduncle.*—Generally smooth.

(7) *Fragrance.*—Absent or weak.

(8) *Length of Stems.*—About 60 cm to 100 cm.

Petals:

(1) *Texture.*—Crisp.

(2) *Appearance.*—Inside variety and outside satiny.

(3) *Form and size.*—Broad, medium, medium undulation of margin.
(4) *Arrangement.*—Regularly arranged, imbricated.
(5) *Petaloids.*—About 15, same color as petals.
(6) *Lasting quality.*—About two weeks on plant, about 12 days after cutting.

REPRODUCTIVE ORGANS

A. Stamens, filaments and anthers:
*Arrangement and color.*—Regularly arranged around styles; color of filaments — red.
B. Pollen:
*Color.*—Near 19A to 19B.
C. Styles: Long, stigma above mouth of receptacle, white.
D. Stigmas: Yellow.
E. Hip: Pitcher-shaped; small seed vessel at petal fall.

PLANT

A. Form: Narrow, bushy, average disease resistance, height about 1.5 m, spread about 0.5 m.
B. Growth: Vigorous.
C. Foliage: Compound 3, 5 and 7 leaflets.
(1) *Size.*—3-leaflet, leaf, terminal leaflet about 7 to 8 cm long; 5-leaflet leaf, terminal leaflet about 8 to 9 cm long; 7 leaflet leaf, terminal leaflet about 8 to 9 cm long.
(2) *Quantity.*—Abundant.
(3) *Color.*—Juvenile foliage — upper side near 187A, under side near 187B; absent or weak anthocyanin coloration, (shoot about 20 cm long); mature leaf color — upper side near 139A, under side near 139B.
(4) *Shape.*—Broad oval.
(5) *Texture.*—Upper side is glossy; underside is matte.
(6) *Edge.*—Serrate.
(7) *Serration.*—Ordinary, acuminate apices.
(8) *Leaf stem.*—Color — dark green with brown cast.
(9) *Stipules.*—Medium, simple, young leaves margin near 177A, middle near 138B; old leaves margin near 139A, middle near 138B.
(10) *Leaflets.*—Cross section — flat: absent or weak medium undulation of margin; terminal leaflet — medium length and medium width; rounded base.
D. Wood:
(1) *New wood.*—Color — young shoots near 177A, have weak anthocyanin; coloration — bronze red purple to reddish brown.
(2) *Old wood.*—Color — brownish green and near 187A.
E. Prickles (thorns):
(1) *Prickles.*—Present; near 181B; quantity (main stalk) few to none; shape of lower side — concave; Length — short prickles absent or very few Position — irregular when they appear.

What is claimed is:

1. A new and distinct rose plant of the variety substantially as shown and described.

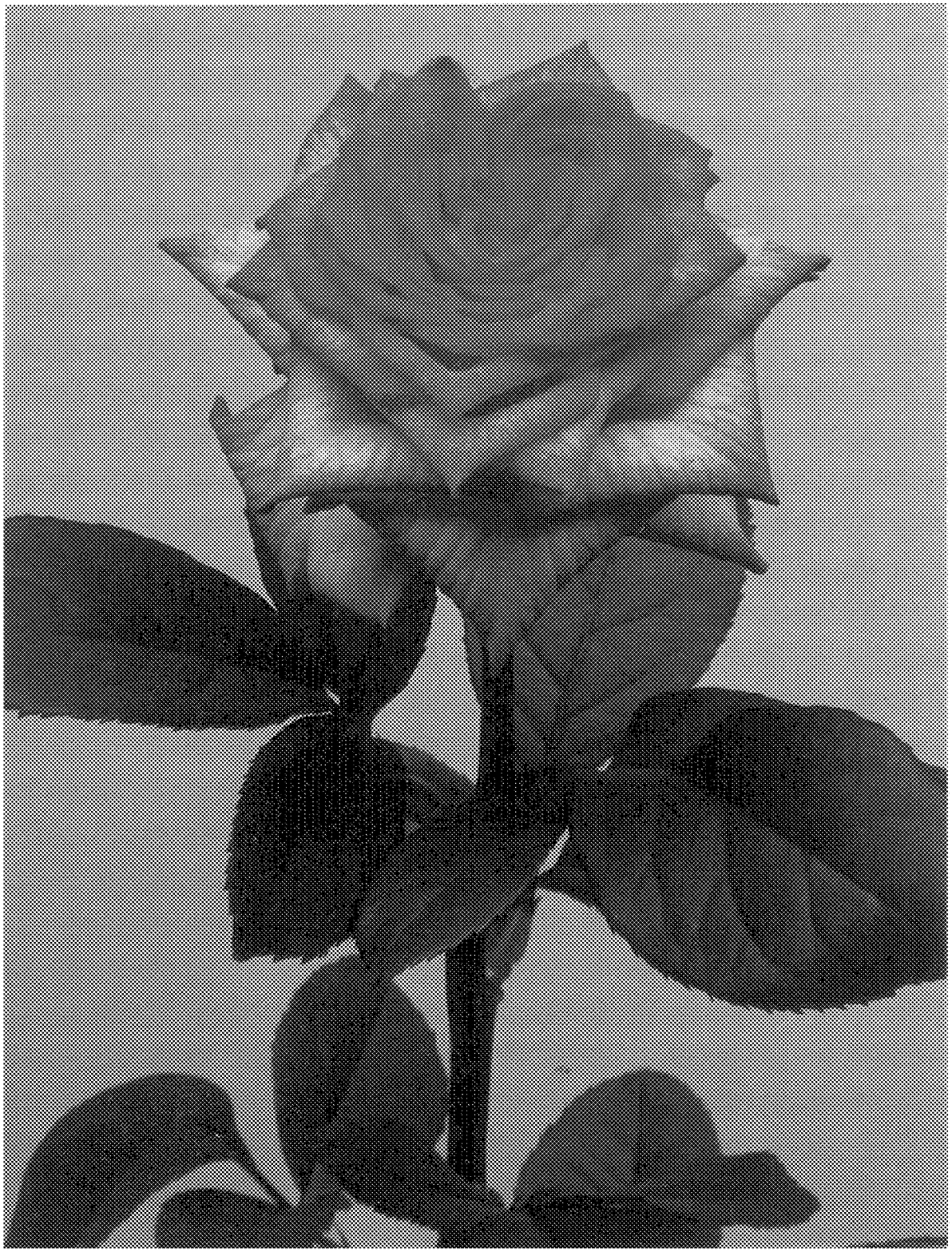

* * * * *